United States Patent [19]
Chapelle et al.

[11] Patent Number: 5,795,903
[45] Date of Patent: Aug. 18, 1998

[54] 6-POLYFLUOROALKOXY-AND 6-POLYFLUOROALKYL-2-AMINOBENZOTHIAZOLE DERIVATIVES

[75] Inventors: Philip Chapelle, Draveil; Claude Gaillard, Thiais; Patrick Jimonet, Villepreux; Erik Louvel; Michel Martinet, both of Paris; Serge Mignani, Chatenay-Malabry; Gérard Sanderink, Saint-Remy-les-Chevreuse, all of France

[73] Assignee: Rhone-Poulenc Rorer S.A., Antony, France

[21] Appl. No.: 817,744

[22] PCT Filed: Oct. 23, 1995

[86] PCT No.: PCT/FR95/01392

§ 371 Date: Apr. 24, 1997

§ 102(e) Date: Apr. 24, 1997

[87] PCT Pub. No.: WO96/13492

PCT Pub. Date: May 9, 1996

[30] Foreign Application Priority Data

Oct. 26, 1994 [FR] France ................ 94 12796

[51] Int. Cl.[6] ................ A61K 31/425; C07D 277/82

[52] U.S. Cl. ................ 514/367; 548/161; 548/164

[58] Field of Search ................ 548/161, 164; 514/367

[56] References Cited

U.S. PATENT DOCUMENTS

| 4,370,338 | 1/1983 | Mizoule. | |
|---|---|---|---|
| 5,008,280 | 4/1991 | Gueremy et al. | 514/367 |
| 5,236,940 | 8/1993 | Audiau et al. | 514/367 |

*Primary Examiner*—Robert W. Ramsues
*Assistant Examiner*—Laura R. C. Lutz
*Attorney, Agent, or Firm*—Finnegan, Henderson, Farabow, Garrett & Dunner, L.L.P.

[57] ABSTRACT

Compounds of formula (I):

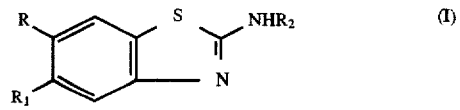

wherein R is a polyfluoroalkoxy or polyfluoroalkyl radical and $R_1$ is a hydrogen atom and $R_2$ is a hydroxyl radical, or $R_1$ is a hydroxyl radical and $R_2$ is a hydrogen atom, salts thereof, the preparation of said compounds, and drugs containing same.

9 Claims, No Drawings

6-POLYFLUOROALKOXY-AND 6-POLYFLUOROALKYL-2-AMINOBENZOTHIAZOLE DERIVATIVES

This application is a 371 of PCT/FR95/01392 filed Oct. 23, 1995.

The present invention relates to compounds of formula:

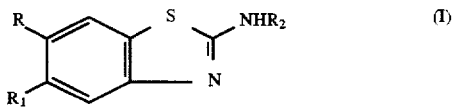

to their salts, to their preparation and to the medicaments containing them.

In the formula (I), R represents a polyfluoroalkoxy or polyfluoroalkyl radical, and either $R_1$ represents a hydrogen atom and $R_2$ represents a hydroxyl radical, or $R_1$ represents a hydroxyl radical and $R_2$ represents a hydrogen atom.

The polyfluoroalkoxy radicals are preferably trifluoromethoxy, pentafluoroethoxy, 2,2,2-trifluoroethoxy and 1,1,2,2-tetrafluoroethoxy radicals. The polyfluoroalkyl radicals are preferably trifluoromethyl radicals.

In the preceding definitions and those which will be mentioned below, the alkyl and alkoxy radicals and portions contain 1 to 4 straight- or branched-chain carbon atoms.

The compounds of formula (I) in which $R_1$ represents a hydrogen atom and $R_2$ represents a hydroxyl radical can be prepared by reacting hydroxylamine hydrochloride with a corresponding 2-chloro-6-(polyfluoroalkoxy)- or -6-(polyfluoroalkyl)benzothiazole.

This reaction is carried out in an inert solvent such as a lower alcohol (for example, methanol), in the presence of a base such as an alkali metal hydroxide (for example, sodium hydroxide or potassium hydroxide), at the boiling temperature of the reaction mixture.

The 2-chloro-6-(polyfluoroalkoxy)- or -6-(polyfluoroalkyl)benzothiazoles can be obtained by application or adaptation of the methods described by S. Mignani et al., Synth. Commun., 22 (19), 2769–2780 (1992) and in the examples.

The compounds of formula (I) in which $R_1$ represents a hydroxyl radical and $R_2$ represents a hydrogen atom can be prepared by demethylation of a corresponding 2-amino-5-methoxy-6-(polyfluoroalkoxy)- or -6-(polyfluoroalkyl)benzothiazole.

This demethylation is generally carried out using excess hydrobromic acid, at the boiling temperature of the reaction mixture.

The 2-amino-5-methoxy-6-(polyfluoroalkoxy)- or -6-(polyfluoroalkyl)benzothiazoles can be obtained by application or adaptation of the methods described in the examples.

The reaction mixtures obtained by the various processes described above are treated according to conventional physical (evaporation, extraction, distillation, chromatography, crystallization, and the like) or chemical (formation of salts, and the like) methods.

The compounds of formula (I) in the free base form can optionally be converted to addition salts with an inorganic or organic acid, by reaction with such an acid in an organic solvent, such as an alcohol, a ketone, an ether or a chlorinated solvent.

The compounds of formula (I), for medicinal purposes, can be used as is or in the form of pharmaceutically acceptable salts, that is to say non-toxic at the use doses.

The addition salts with inorganic or organic acids, such as acetate, propionate, succinic, benzoate, fumarate, maleate, oxalate, methanesulphonate, isethionate, theophyllinacetate, salicylate, methylenebis-β-oxynaphthoate, hydrochloride, sulphate, nitrate and phosphate, may be mentioned as examples of pharmaceutically acceptable salts.

The compounds of formula (I) and their salts exhibit advantageous pharmacological properties. These compounds interfere with glutamatergic transmission and are therefore useful in the treatment and the prevention of phenomena related to glutamate. These phenomena are in particular epileptogenic and/or convulsive manifestations, schizophrenic disorders, sleep disorders, anxiety, phenomena related to cerebral ischaemia, and neurodegenerative diseases and neurological disorders related to aging where glutamate may be involved, such as Alzheimer's disease, Parkinson's disease, Huntington's chorea, amyotrophic lateral sclerosis, cranial and medullary traumas and olivopontocerebellar atrophy.

The antiglutamate activity of these products was determined with respect to convulsions induced by glutamate according to a technique inspired by that of I. P. Lapin, J. Neural. Transmission, 54, 229–238 (1982); injection of glutamate by the intracerebroventricular route being carried out according to a technique inspired by that of R. Chermat and P. Simon, J. Pharmacol. (Paris), 6, 489–492 (1975). Their $ED_{50}$ is less than 10 mg/kg.

The compounds of formula (I) exhibit low toxicity. Their $LD_{50}$ is greater than 55 mg/kg by the IP route in mice.

The preferred compounds of formula (I) are the following:

2-hydroxyamino-6-(trifluoromethoxy)benzothiazole, 2-amino-5-hydroxy-6-(trifluoromethoxy)benzothiazole, 2-hydroxyamino-6-(trifluoromethyl)benzothiazole and their salts.

The following examples illustrate the invention.

EXAMPLE 1

21.81 g of hydroxylamine hydrochloride are added to 17.61 g of potassium hydroxide in solution in 350 ml of methanol at a temperature in the region of 20° C. and the reaction mixture is brought to reflux for 10 minutes. 13.24 g of 2-chloro-6-(trifluoromethoxy)benzothiazole are then added and the reaction is continued at reflux for 5 hours. After cooling to a temperature in the region of 20° C., the precipitate formed is filtered off and the filtrate concentrated to dryness under reduced pressure (15 mm Hg, 2 kPa). The crude product thus obtained is purified by flash chromatography on a silica column, using an ethyl acetate/cyclohexane (20/80 by volume) mixture as eluent. 7.35 g of 2-hydroxyamino-6-(trifluoromethoxy)benzothiazole are thus isolated in the form of an orangey-yellow powder melting with decomposition at 119° C. [(Analysis % calculated C: 38.40, H: 2.01, F: 22.78, N: 11.20, S: 12.82; % found C: 38.7, H: 1.9, F: 22.3, N: 11.1, S: 12.6); $^1$H N.M.R. spectrum (250 MHz, d6-$(CD_3)_2SO$, at a temperature of 373 K, δ in ppm): 7.22 (mt, 2H, H 4 and H 5), 7.62 (broad s, 1H, H 7), 9.55 and from 9.50 to 11.00 (respectively broad s and unresolved peak, each 1H, NHOH)].

2-Chloro-6-(trifluoromethoxy)benzothiazole can be prepared according to the process described by S. Mignani et al., Synth. Commun., 22(19), 2769–2780 (1992).

EXAMPLE 2

0.74 g of 2-amino-5-methoxy-6-(trifluoromethoxy) benzothiazole, in solution in 20 ml of 47% hydrobromic acid, are brought to reflux for 20 hours. After cooling to a temperature in the region of 20° C., the reaction mixture is poured in 20 ml of ice-cold water and the solution is basified using concentrated sodium hydroxide. The organic phase is then extracted with ethyl acetate, dried over magnesium sulphate, filtered and concentrated to dryness under reduced pressure (15 mm Hg, 2 kPa). The crude product thus obtained is purified by flash chromatography on a silica column, a dichloromethane/methanol (98/2 by volume) mixture being used as eluent. 0.49 g of 2-amino-5-hydroxy-6-(trifluoromethoxy)benzothiazole are thus isolated in the form of a white powder melting at 216° C. [(Analysis % calculated C: 38.40, H: 2.01, F: 22.78, N: 11.20, S: 12.82; % found C: 38.3, H: 1.9, F: 22.9, N: 11.2, S: 13.0); $^1$H N.M.R. spectrum (250 MHz, d6-$(CD_3)_2SO$, δ in ppm): 6.96 (broad s, 1H, aromatic H ortho to the OH), 7.54 (broad s, 2H, $NH_2$), 7.61 (broad s, 1H, aromatic H meta to the OH), 9.95 (unresolved peak, 1H, OH)].

2-Amino-5-methoxy-6-(trifluoromethoxy)benzothiazole can be prepared according to the following method: 1.5 g of potassium thiocyanate are added in a single step to 0.8 g of 3-methoxy-4-(trifluoromethoxy)aniline in solution in 10 ml of acetic acid. After stirring for 20 minutes at a temperature in the region of 20° C., a solution of 0.21 ml of bromine in 5 ml of acetic acid is added dropwise to the reaction mixture over approximately 30 minutes. The reaction is continued for 15 hours at the same temperature and the reaction mixture is then diluted with 15 ml of distilled water and neutralized using concentrated sodium hydroxide. The organic phase is extracted with ethyl acetate, washed with water, dried and concentrated to dryness. The crude product thus obtained is purified by flash chromatography on a silica column, a dichloromethane/methanol (90/10 by volume) mixture being used as eluent. 0.74 g of the expected product are obtained in the form of a yellow powder melting at 153° C. [$^1$H N.M.R. spectrum (300 MHz, d6-$(CD_3)_2SO$, δ in ppm): 3.87 (s, 3H, $OCH_3$), 7.16 (s, 1H, aromatic H ortho to the $OCH_3$), 7.62 (broad s, 2H, $NH_2$), 7.73 (broad s, 1H, aromatic H meta to the $CH_3$)].

3-Methoxy-4-(trifluoromethoxy)aniline can be obtained according to the following procedure: 0.5 g of 3-methoxy-4-(trifluoromethoxy)nitrobenzene, in solution in 10 ml of methanol, are hydrogenated at atmospheric pressure and at a temperature in the region of 20° C. in the presence of 10 mg of platinum oxide. After absorption of the theoretical volume of hydrogen, the reaction mixture is filtered through Celite and the filtrate concentrated to dryness under reduced pressure. The crude product is purified by filtration through silica, an ethyl acetate/cyclohexane (50/50 by volume) mixture being used as eluent. 0.4 g of the expected product is thus obtained in the form of a yellow oil [$^1$H N.M.R. spectrum (200 MHz, d6-$(CD_3)_2SO$, δ in ppm): 3.76 (s, 3H, $OCH_3$), 5.33 (broad s, 2H, $NH_2$), 6.16 (dd, J=9 and 2.5 Hz, 1H, aromatic H para to the $OCH_3$), 6.39 (d, J=2.5 Hz, 1H, aromatic H ortho to the $OCH_3$), 6.96 (broad d, J=9 Hz, 1H, aromatic H meta to the $OCH_3$)].

3-Methoxy-4-(trifluoromethoxy)nitrobenzene can be prepared according to the following procedure: 0.66 ml of dimethyl sulphate is added to 1.3 g of 2-trifluoromethoxy-5-nitrophenol in 6 ml of ethanol brought to 50° C. and then an aqueous sodium hydroxide solution, prepared from 0.28 g of sodium hydroxide pellets and 3 ml of distilled water, is added. The reaction mixture is heated at reflux for 4 hours. After cooling to a temperature in the region of 20° C., 10 ml of distilled water are added to the reaction mixture and the organic phase is extracted with dichloromethane. The crude product obtained by the usual treatment is purified by flash chromatography on a silica column, a dichloromethane/cyclohexane (20/80 by volume) mixture being used as eluent. 0.5 g of the expected product is thus obtained in the form of a yellow oil [$^1$H N.M.R. spectrum: (200 MHz, d6-$(CD_3)_2SO$, δ in ppm: 4.01 (s, 3H, $OCH_3$), 7.70 (broad d, J=9 Hz, 1H, aromatic H meta to the $OCH_3$), 7.96 (dd, J=9 and 2.5 Hz, 1H, aromatic H para to the $OCH_3$), 8.04 (d, J=2.5 Hz, 1H, aromatic H ortho to the $OCH_3$)].

2-Trifluoromethoxy-5-nitrophenol can be prepared according to the following method: an aqueous sodium nitrite (0.82 g) solution (2 ml) is added dropwise to a suspension of 2.35 g of 2-trifluoromethoxy-5-nitroaniline in 17 ml of distilled water cooled to 5° C. and in the presence of 5 ml of concentrated hydrochloric acid. After stirring for 30 minutes at the same temperature, an aqueous sodium tetrafluoroborate (1.66 g) solution (5 ml) is added dropwise to the reaction mixture, which has become clear. After reacting for 30 minutes, still at the same temperature, the precipitate formed is filtered off, washed with water and dried. 1.85 g of 2-trifluoromethoxy-5-nitrophenyldiazonium tetrafluoroborate are thus obtained in the form of a white powder used without additional purification in the subsequent syntheses. This diazonium salt is then divided into 4 portions of approximately 0.5 g. Each portion is added to a solution of 150 g of copper nitrate (trihydrate) in 100 ml of distilled water. 0.15 g of copper oxide are then added and the reaction is continued for 30 minutes at a temperature in the region of 20° C. After filtering off the insoluble material on a Celite bed and washing with dichloromethane, the organic phase is extracted from the filtrate with dichloromethane and the 4 organic phases are combined and concentrated to dryness under reduced pressure. The crude product (1 g of brown oil) is purified by flash chromatography on a silica column, an ethyl acetate/cyclohexane (10/90 by volume) mixture being used as eluent. 0.4 g of the expected phenol is thus obtained in the form of a pale yellow powder [$^1$H N.M.R. spectrum (200 MHz, d6-$(CD_3)_2SO$, δ in ppm): 7.61 (broad d, J=9 Hz, 1H, aromatic H meta to the OH), 7.78 (dd, J=9 and 2.5 Hz, 1H, aromatic H para to the OH), 7.86 (d, J=2.5 Hz, 1H, aromatic H ortho to the OH), 11.38 (broad unresolved peak, 1H, OH)].

2-Trifluoromethoxy-5-nitroaniline can be prepared according to the following procedure: 10 g of 2-(trifluoromethoxy)aniline are added progressively to 280 ml of concentrated sulphuric acid cooled to 0° C. and then 5.7 g of potassium nitrate are added in small portions. The reaction is continued for 2 hours at the same temperature. The reaction mixture is then run onto 1 liter of ice and then diluted with 3 liters of distilled water. Extraction of the organic phase with three times 500 ml of ethyl ether leads, after drying over magnesium sulphate, filtration and concentration to dryness under reduced pressure, to 10.9 g of the expected product in the form of a yellow solid melting at 88° C. [$^1$H N.M.R. spectrum (200 MHz, $CDCl_3$, δ in ppm): 4.00 (unresolved peak, 2H, $NH_2$), 7.18 (broad d, J=9 Hz, 1H, aromatic H meta to the $NH_2$), 7.52 (dd, J=9 and 2.5 Hz, 1H, aromatic H para to the $NH_2$), 7.60 (d, J=2.5 Hz, 1H, aromatic H ortho to the $NH_2$)].

EXAMPLE 3

0.88 g of hydroxylamine hydrochloide is added to a solution of 0.7 g of potassium hydroxide in 15 ml of methanol and the reaction mixture is brought to reflux for 10 minutes. 0.5 g of 2-chloro-6-(trifluoromethyl)benzothiazole is then added and reflux is continued for 8 hours. After cooling to a temperature in the region of 20° C., the insoluble material is filtered off, the filtrate concentrated to dryness and the residue taken up in dichloromethane. The organic phase is washed with water and then dried and concentrated to dryness under reduced pressure (15 mm Hg, 2 kPa). The crude product thus obtained is purified by flash chromatography on a silica column, an ethyl acetate/ cyclohexane (40/60 by volume) mixture being used as eluent. 0.35 g of 2-hydroxyamino-6-(trifluoromethyl) benzothiazole is thus obtained in the form of an orangey powder, the melting point of which is greater than 260° C. (Analysis % calculated C: 41.03, H: 2.15, N: 11.96, S: 13.69; found C: 41.4, H: 1.6, N: 12.3, S: 13.9) [$^1$H N.M.R. spectrum (200 MHz, d6-(CD$_3$)$_2$SO, δ in ppm): 7.2 (broad s, 1H, aromatic CH), 7.53 (d, J=7 Hz, aromatic CH, 8.0 (broad s, 1H, aromatic CH), 10.07 (s, 1H, NH, 11.05 (s, 1H, OH)].

2-Chloro-6-(trifluoromethyl)benzothiazole can be prepared according to the following procedure: a solution of 3 g of sodium nitrite in 5 ml of distilled water is added dropwise to a solution of 5 g of 2-amino-6-(trifluoromethyl) benzothiazole in 17 ml of 6N hydrochloric acid cooled to 0° C. and stirring is continued at the same temperature for 2 hours. The reaction mixture is then treated with 13.8 g of cuprous chloride and the reaction is continued for 4 hours at a temperature in the region of 20° C. The reaction mixture is then poured onto 150 ml of ice-cold water and the insoluble material is filtered off, then taken up in dichloromethane and the new insoluble material isolated. The filtrate is washed with water and this organic phase is then dried and concentrated to dryness under reduced pressure (15 mm Hg, 2 kPa). The crude product is purified by flash chromatography on a silica column, a cyclohexane/ dichloromethane (95/5 by volume) mixture being used as eluent. 1.47 g of the expected product are thus obtained in the form of a yellow foam [$^1$H N.M.R. spectrum (300 MHz, d6-(CD$_3$)$_2$SO, δ in ppm): 7.91 (d, J=7 Hz, 1H, aromatic CH), 8.20 (d, J=7 Hz, 1H, aromatic CH), 8.7 (s, 1H, aromatic CH)].

2-Amino-6-(trifluoromethyl)benzothiazole can be obtained according to the method described in U.S. Pat. No. 2,822,359.

The medicaments according to the invention consist of a compound of formula (I) in the free form or in the form of an addition salt with a pharmaceutically acceptable acid, in the pure state or in the form of a composition in which it is combined with any other pharmaceutically compatible product, which can be inert or physiologically active. The medicaments according to the invention may be employed orally, parenterally, intravenously, rectally or topically.

As solid compositions for oral administration, tablets, pills, powders (gelatin capsules, cachets) or granules may be used. In these compositions, the active principle according to the invention is mixed with one or a number of inert diluents, such as starch, cellulose, sucrose, lactose or silica, under an argon stream. These compositions can also comprise substances other than diluents, for example one or a number of lubricants such as magnesium stearate or talc, a colouring, a coating (dragées) or a varnish.

As liquid compositions for oral administration, pharmaceutically acceptable solutions, suspensions, emulsions, syrups and elixirs containing inert diluents such as water, ethanol, glycerol, vegetable oils or liquid paraffin may be used. These compositions can contain substances other than diluents, for example wetting, sweetening, thickening, flavouring or stabilizing products.

The sterile compositions for parenteral administration can preferably be suspensions, emulsions or aqueous or nonaqueous solutions. As solvent or vehicle, water, propylene glycol, a polyethylene glycol, vegetable oils, especially olive oil, injectable organic esters, for example ethyl oleate, or other suitable organic solvents may be employed. These compositions can also contain adjuvants, especially wetting, tonicity, emulsifying, dispersing and stabilizing agents. Sterilization may be carried out in several ways, for example by aseptic filtration, by incorporating sterilizing agents in the composition, by irradiation or by heating. They can also be prepared in the form of sterile solid compositions which can be dissolved at the time of use in sterile water or any other sterile injectable medium.

The compositions for rectal administration are suppositories or rectal capsules which contain, apart from the active product, excipients such as cocoa butter, semi-synthetic glycerides or polyethylene glycols.

The compositions for topical administration can be, for example, creams, lotions, eyewashes, mouthwashes, nose drops or aerosols.

In human therapy, the compounds according to the invention interfere with glutamatergic transmission and are thus particularly useful in the treatment and the prevention of disorders related to glutamate. These compounds are in particular useful for the treatment or the prevention of epileptogenic and/or convulsive manifestations, schizophrenic disorders, sleep disorders, anxiety, phenomena related to cerebral ischaemia, and neurodegenerative disorders and neurological disorders related to aging where glutamate may be involved, such as Alzheimer's disease, Parkinson's disease, Huntington's chorea, amyotrophic lateral sclerosis, cranial and medullary traumas and olivopontocerebellar atrophy.

The doses depend on the effect sought, the duration of the treatment and the administration route used; they are generally between 30 and 300 mg per day for an adult, administered orally, with single doses ranging from 10 to 100 mg of active substance.

Generally speaking, the doctor will determine the appropriate dosage in accordance with the age, weight and all the other factors specific to the patient to be treated.

The following examples illustrate compositions according to the invention:

EXAMPLE A

Gelatin capsules containing 50 mg of active product and having the following composition are prepared according to the usual technique:

Compound of formula (I) . . . 50 mg

Cellulose . . . 18 mg

Lactose . . . 55 mg

Colloidal silica . . . 1 mg

Sodium carboxymethyl starch . . . 10 mg

Talc . . . 10 mg

Magnesium stearate . . . 1 mg

EXAMPLE B

Tablets containing 50 mg of active product and having the following composition are prepared according to the usual technique:

Compound of formula (I) . . . 50 mg

Lactose . . . 104 mg

Cellulose . . . 40 mg

Polyvidone . . . 10 mg

Sodium carboxymethyl starch . . . 22 mg

Talc . . . 10 mg

Magnesium stearate . . . 2 mg

Colloidal silica . . . 2 mg

Mixture of hydroxymethylcellulose, glycerol and titanium oxide (72/3.5/24.5) . . . q.s. for 1 finished coated tablet 245 mg

EXAMPLE C

An injectable solution containing 10 mg of active product and having the following composition is prepared:

Compound of formula (I) . . . 10 mg

Benzoic acid . . . 80 mg

Benzyl alcohol . . . 0.06 cm$^3$

Sodium benzoate . . . 80 mg

95% Ethanol . . . 0.4 cm$^3$

Sodium hydroxide . . . 24 mg

Propylene glycol . . . 1.6 cm$^3$

Water . . . q.s. for 4 cm$^3$

We claim:

1. A compound of formula (I):

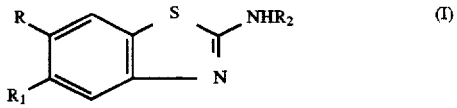

in which R represents a polyfluoroalkoxy or polyfluoroalkyl radical, and either $R_1$ represents a hydrogen atom and $R_2$ represents a hydroxyl radical, or $R_1$ represents a hydroxyl radical and $R_2$ represents a hydrogen atom;

it being understood that the alkoxy and alkyl portions of said radicals contain 1 to 4 straight- or branched-chain carbon atoms, and the salts of said compound of formula (I).

2. A compound according to claim 1, in which R represents a trifluoromethoxy, pentafluoroethoxy, 2,2,2-trifluoroethoxy, 1,1,2,2-tetrafluoroethoxy or trifluoromethyl radical.

3. A compound of formula (I), said compound being:

2-hydroxyamino-6-(trifluoromethoxy)benzothiazole, 2-amino-5-hydroxy-6-(trifluoromethoxy)benzothiazole, 2-hydroxyamino-6-(trifluoromethyl)benzothiazole, or a salt thereof.

4. A process for preparing a compound of formula (I) according to claim 1 in which $R_1$ represents a hydrogen atom and $R_2$ represents a hydroxyl radical, wherein said process comprises reacting hydroxylamine hydrochloride with a 2-chloro-6-(polyfluoroalkoxy)- or -6-(polyfluoroalkyl)-benzothiazole, isolating the product of said reaction, and optionally converting said isolated product to a salt.

5. A process for preparing a compound of formula (I) according to claim 1 in which $R_1$ represents a hydroxyl radical and $R_2$ represents a hydrogen atom, wherein said process comprises demethylating 2-amino-5-methoxy-6-(polyfluoroalkoxy)- or -6-(polyfluoroalkyl)benzothiazole, isolating the product of said demethylation, and optionally converting said isolated product to a salt.

6. A pharmaceutical composition comprising a pharmaceutically effective amount of at least one compound of formula (I) according to claim 1 or a pharmaceutically acceptable salt thereof, and a pharmaceutically acceptable carrier.

7. A pharmaceutical composition comprising a pharmaceutically effective amount of at least one compound of formula (I) according to claim 2 or a pharmaceutically acceptable salt thereof, and a pharmaceutically acceptable carrier.

8. A pharmaceutical composition comprising a pharmaceutically effective amount of at least one compound of formula (I) according to claim 3 or a pharmaceutically acceptable salt thereof, and a pharmaceutically acceptable carrier.

9. A method for treating epileptogenic and/or convulsive manifestations, schizophrenic disorders, sleep disorders, anxiety, phenomena related to cerebral ischaemia, Alzheimer's disease, Parkinson's disease, Huntington's chorea, amyotrophic lateral sclerosis, cranial and medullary traumas and olivopontocerebellar atrophy, said method comprising administering to a host in need of said treatment or prevention an effective amount of a compound of formula (I) or a pharmaceutically acceptable salt thereof as claimed in claim 1.

* * * * *